United States Patent [19]

Campestrini et al.

[11] Patent Number: 4,859,799

[45] Date of Patent: Aug. 22, 1989

[54] PROCESS FOR THE PRODUCTION OF ALDEHYDE OR KETONE COMPOUNDS AND ALDEHYDES AND KETONES OBTAINED BY MEANS OF THIS PROCESS

[75] Inventors: Sandro Campestrini, Trent; Fulvio Di Furia, Padua; Giorgio Modena, Padua; Lucia Pasquato, Padua, all of Italy

[73] Assignee: Interox (Société Anonyme), Brussels, Belgium

[21] Appl. No.: 196,826

[22] Filed: May 20, 1988

Related U.S. Application Data

[63] Continuation of Ser. No. 905,325, Sep. 9, 1986, abandoned.

[30] Foreign Application Priority Data

Sep. 9, 1985 [IT] Italy .................. 22092 A/85

[51] Int. Cl.$^4$ .............................................. C07C 45/27
[52] U.S. Cl. ............................... 568/430; 568/485; 568/311; 568/342; 568/385
[58] Field of Search ............ 568/430, 311, 485, 342, 568/385

[56] References Cited

U.S. PATENT DOCUMENTS

| | | | |
|---|---|---|---|
| 3,972,944 | 8/1976 | Waldmann et al. | 568/430 |
| 3,992,432 | 11/1976 | Napier et al. | 568/430 |
| 4,104,312 | 8/1978 | Angstadt et al. | 568/385 |
| 4,152,354 | 5/1979 | Stapp | 568/401 |
| 4,171,313 | 10/1979 | Mares et al. | 568/311 |
| 4,293,717 | 10/1981 | Waldmann et al. | 568/485 |
| 4,609,765 | 9/1986 | Neri et al. | 568/430 |

FOREIGN PATENT DOCUMENTS

| | | | |
|---|---|---|---|
| 097551 | 1/1984 | European Pat. Off. | 568/401 |
| 2489710 | 3/1982 | France | 564/400 |

OTHER PUBLICATIONS

Mimoun, H., "Nouveauz complexes", 1969 Bull. Soc. Chim. France No. 5, pp. 1481–1492, No. 267.

Mimoun, H., "Epoxydation des olefines", Tetrahedron, vol. 26, 1970, pp. 37–50.

*Primary Examiner*—James H. Reamer
*Attorney, Agent, or Firm*—Spencer & Frank

[57] ABSTRACT

Process for the production of aldehydes or ketones by oxidative cleavage of olefinic double bonds by means of a coordination complex of a ligand and a peroxo derivative of a metal of group 6b.

Aldehydes and ketones obtained by said process are used among others as intermediates in the synthesis of organic products.

13 Claims, No Drawings

PROCESS FOR THE PRODUCTION OF ALDEHYDE OR KETONE COMPOUNDS AND ALDEHYDES AND KETONES OBTAINED BY MEANS OF THIS PROCESS

This application is a continuation of application Ser. No. 905,325, filed Sept. 9, 1986.

BACKGROUND OF THE INVENTION

The present invention relates to a process for the production of organic compounds of the group of aldehydes and ketones. In particular, it relates to the production of aldehydes or ketones from olefins by treatment thereof with an oxidising agent.

It is known fact that methylketones can be obtained by the oxidation of terminal olefins with molecular oxygen in the presence of cationic complexes of rhodium III used as catalysts (*JOURNAL OF MOLECULAR CATALYSIS*, Vol. 7, January, 1980, Lausanne, H. Mimoun "The Role of Peroxymetallation in Selective Oxidative Processes", page 1 to 29, *page 12 and 13*).

For the production of methylketones, it has also been proposed to selectively oxidise the terminal olefins with palladium II tertiary butyl peroxide carboxylates (*AMERICAN CHEMICAL SOCIETY*, Vol. 102, n° 3, 30 January 1980, Washington D.C., H. Mimoun, R. Charpentier, A. Mitschler, J. Fischer and R. Weiss "Palladium II tert-Butyl Peroxide Carboxylates. New reagents for the Selective Oxidation of Terminal Olefins to Methyl Ketones. On the Role of Peroxymetallation in Selective Oxidative Processes", page 1047 to 1054, *page 1048 and 1049*).

However, these well known processes do not make it possible to obtain aldehydes or ketones other than those belonging to the class of methylketones. Moreover, these have the disadvantage of requiring an anhydrous medium; otherwise, the reaction is inhibited or else metal precipitation occurs. The rhodium complexes also require the presence of an alcohol in the reaction medium.

It is also known that oxidative splitting of the C=C double bonds of the olefins can be effected by means of ruthenium tetroxide to give carbonyl derivatives (W. S. Trahanocsky "*Oxidation in Organic Chemistry*, part B, 1973, ACADEMIC PRESS, New York, page 177 to 227: D. G. Lee and M. Van Den Engh, "Oxidation by Ruthenium Tetroxide" *page 186 to 192*).

However, this known process has the disadvantage of giving poor selectivity: all the different types of carbonyl derivatives (aldehydes, ketones and acids) are produced together and in mixture with products from concurrent reactions not involving the cleavage of the double bond (diols).

SUMMARY OF THE INVENTION

The present invention overcomes these disadvantages of the known processes by carrying out a new process for the selective production of aldehyde or ketone compounds free from acid and diols which does not necessarily require the presence of an alcohol, which is not inhibited by the presence of water even in quantities exceeding its solubility in the organic reaction medium and which gives the ketones $R_1$—CO—$R_2$ where the $R_1$ and $R_2$ groups can both contain more than 1 carbon atom.

In this connection, the present invention relates to a process for the production of organic aldehyde or ketone compounds from olefins, according to which an oxidative cleavage of the double bond of the olefin is effected by means of a coordination complex of a ligand and a peroxo derivative of a metal of group 6b using controlled quantities of olefin and complex such that the molar ratio of olefin to active oxygen of the complex is between 0.1 and 0.5.

According to the present invention the expression organic aldehyde compound is intended to indicate an organic carbonyl compound with the general formula

where the R group combined with the aldehyde radical represents a hydrogen atom or a linear or branched aliphatic chain which may be unsubstituted or substituted by one or more functional groups (e.g. the nitrile groups, halogen, alcohol, amine, amide, ether and sulphonate), a monocyclic or polycyclic aromatic group which may be unsubstituted or substituted by one or more functional groups (such as those described above), a monocyclic or polycyclic cyclane group which may be unsubstituted or substituted, a group of the class of the substituted or unsubstituted spiranes or a combination of two or more of such groups.

The expression organic ketone compound is intended to indicate an organic carbonyl compound with the general formula $R_1$–CO–$R_2$ in which $R_1$ and $R_2$ represent the same groups as defined above for group R of the aldehyde and they can all contain more than 1 carbon atom.

According to the present invention, olefin is intended to indicate organic compounds which contain at least 1 carbon-carbon double bond such as the following:

aliphatic mono-olefins containing 2–30 carbon atoms and which may carry substituents which do not interfere with the epoxidation reactions, e.g. the halogens of allyl halides and the hydroxides of allyl alcohols;

cycloaliphatic mono-olefins containing 4–20 carbon atoms and which may carry substituents which do not interfere with the oxidative cleavage reaction;

polycyclic systems containing double ethylene bonds;

polyolefins containing ethylene unsaturations.

Examples of such olefins are ethylene, propylene, 1-butene, 2-butene, isobutene, butadiene, pentenes and in particular 1-pentene, 2-methyl-1-butene, 3-methyl-1-butene, 2-methyl-2-butene, piperyline, 1,2 and 3-hexens, hexadienes, 2,3-dimethyl-2-butene, 1-heptene, 3-ethylpentene-2, 1-octene, diisobutylene, 2,4,4-trimethylpentene-1 and 2, octadienes, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, propylene trimers and tetramers, polybutadienes, isoprene and terpenes such as for example terpinenes, limonene, terpinolene, sabinene, pinene, camphene, mircene, cadinene, cedrene, santalene, calarene, colophene and polyterpene and also their derivatives such as geraniol, linalool and linalyl acetate, methylene cyclopropane, cyclopentene and its derivatives substituted with alkyl or aryl groups, cyclopentadiene, cyclohexene and its derivatives substituted by alkyl and aryl groups, methylene cyclopentane, cyclohexadiene, methylene cyclohexane, norbornene, cycloheptene, vinylcyclohexane, vinylcyclohexene, styrene, cyclooctene, cyclooctadiene, vinylnorbornene, substituted or unsubstituted indene, tetrahydroindene, alpha-methylstyrene and the alpha-alkylstyrenes which may be substituted at the aromatic nucleus, dicyclopetadiene, divinylbenzene, substituted or unsubstituted dihydronaphthalene, cyclodenene, cyclododecatrene, stilbene, 2,3-diphenyl-2-butene, diphenyl butadiene, unsaturated carboxylic acids of any type such as acrylic acid, methacrylic acid, alpha- and beta-cyanoacrylic acids and their derivatives, crotonic acid, maleic acid and their alkylated derivatives, vinylacetic acid and unsaturated fatty acids, amongst which are included in particular the oleic, linoleic, parmitoleic, linolenic, vaccinic, gadoleic, ricinoleic and eleostearic acids and natural fats and oils contained in them and also esters of these unsaturated acids such as alkyl acrylates and methacrylates, diallylmaleate, methyl-7-hydroxy-5-heptanoate, methyloleate and esters of unsaturated alcohols, for example allyl carbonate, diallylphthalate, allylacetate.

According to the present invention, oxidative cleavage of the olefin double bond is effected by means of a coordination complex of a ligand and a peroxo derivative of a metal of group 6b of the periodic table.

The term oxidative cleavage of the olefin double bond is to indicate a rupture of the olefin double bond and a simultaneous oxidation of any of its carbon atoms by forming two carbonyl compounds according to the reaction scheme:

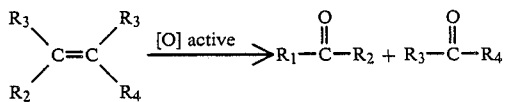

In this reaction scheme: $R_1$, $R_2$, $R_3$ and $R_4$ each indicate a hydrogen atom or a carbon atom group.

According to the present invention, the coordination complex of a ligand and a peroxo derivative of a metal of group 6b is a compound with the general formula:

$M(O_2)_n L_m O_x$ where M represents the metal of group 6b

L indicates the ligand
O is an oxygen atom
x is an integer which can vary between 0 and 2
m is an integer which can vary between 1 and 6
and n is an integer which may vary between 1 and 3.

Examples of coordination complexes of a ligand and peroxo derivative of a metal of group 6b suitable for the process according to the present invention are compounds with the formula:

where M represents the metal of group 6b
L indicates the ligand and
O is an oxygen atom.

DESCRIPTION OF THE PREFERRED EMBODIMENTS

Preferred complexes according to the scope of the present invention are the coordination complexes of a ligand with oxodiperoxo derivates of a metal of group 6b, valency 6, having the formula

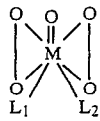

where M indicates the metal of group 6b
$L_1$ indicates $H_2O$ or an organic ligand and
$L_2$ indicates an organic coordinate ligand Among these complexes, those are preferred in which M indicates molybdenum or tungsten.

These complexes are easily prepared by the reaction, in an aqueous solution, of an anhydride or an acid or a metal of group 6b with hydrogen peroxide to give the oxo-diperoxo derivative whereupon the solution containing the compound is brought into contact with the ligand as such or in solution in an organic solvent.

According to the present invention, the ligand used can advantageously be selected among the following classes:

Class 1: tertiary amides
Class 2: phosphoramides
Class 3: aliphatic and aromatic tertiary amine oxides
Class 4: phosphine oxides and
Class 5: aromatic amines.

As examples of ligands belonging to these classes which are suitable for the process according to the present invention, the following can be cited without limiting the scope:

Class 1: dimethyl formamide, dimethyl acetamide and tetramethyl urea

Class 2: hexamethyl phosphotriamide, hexaethyl phosphotriamide, hexabutyl phosphotriamide, tridodecyl phosphotriamide and octamethyl pyrophosporamide Class 3: pyridine oxide, 4-picoline oxide, trioctylamine oxide and phenylpropyl pyridine oxide Class 4: trimethyl phosphine oxide Class 5: pyridine and 2,2'-bipyridine.

The respective proportions of olefin and peroxo complex which are suitable for use depend on a large number of parameters among which feature in particular the nature of the olefin and that of the ligand, the temperature and the pressure maintained during the reaction. However, in order to ensure a substantial yield of aldehyde or ketone, it is necessary for the molar ratio of olefin to be oxidised to active oxygen provided by the peroxo complex not to exceed a value of 0.5. Good results have been obtained when this molar ratio was between 0.1 and 0.5. The best results have been those where this molar ratio was between 0.5 and 0.35.

According to a special embodiment of the process according to the present invention oxidative cleavage is effected in a homogeneous phase in solution in an organic solvent. With this method of execution, the peroxo complex is first prepared by reaction in aqueous solution between hydrogen peroxide, the compounds of the metal of group 6h and the ligand in concentrations such that the peroxo complex forms precipitates and can be isolated by filtration and desiccation. This complex is then dissolved in the reaction mixture consisting of a solution of the olefin to be oxidised in an appropriate organic solvent. As appropriate solvent, any solvent can be used which is in a position to dissolve simultaneously the olefin and the peroxo complex. Examples of such solvents are benzene, toluene, xylene and alkyl-substituted derivatives thereof; dichloromethane, trichloromethane, 1-chloroethane, 1,1-dichloroethane, 1,2-dichloroethane, 1,1,2,2-tetrachloroethane, 1-chloropropane, 2-chloropropane, 1,1-dichloropropane, 1,3-dichloropropane, 2,2-dichloropropane, 1,1,1-trichloropropane, 1,1,2-trichloropropane, 1,1,3-trichloropropane, 1,2,2-trichloropropane, 1,2,3-trichloropropane, tetrachloropropane; halogenated butane, halogenated pentane, halogenated hexane, hydrocarbons whose number of carbon atoms exceeds 6 substituted with one or more halogen atoms; chlorinated aromatic hydrocarbons such as chlorobenzene and linear or branched aliphatic hydrocarbons with preferably between 5 and 8 carbon atoms.

According to this method of executing the process according to the present invention, the reaction period and temperature are variable and depend on various factors, in particular the nature of the olefin and the steric hindrance of the structure of its molecule, the type of peroxo complex used an in particular the nature of the coordination ligand and also the pressure at which the reaction is carried out. These must be determined accurately in each particular case by means of laboratory experiements. For obvious economic reasons it is generally preferable to operate at atmospheric pressure. More specifically, a temperature is chosen which is below the boiling point of the organic solvent at the pressure selected. The period can be between a few minutes and several hours.

According to another embodiment of the process according to the present invention which is preferred, the oxidative cleavage is carried out by adopting the known technique of catalysis by phase transfer. By definition, according to this technique, the ability of certain catalysts (in the present case the complex of the metal of group 6b with the ligand) is exploited to change into an active derivative in one of the two phases, to subsequently pass into the other phase in which the substrate is in solution and to promote the reaction by changing again into their inactive form subsequent to which they return to the first phase in which they undergo once more the change into the active derivative and thus undergo in succession a very large number of successive cycles which depend only on the intrinsic stability of the two forms of catalyst, namely the active and the inactive form.

When this method of preferred execution of the process according to the present invention is carried out, the two phases which are brought together are, on the one hand, an organic phase not miscible with water which contains the olefin and, on the other hand, an aqueous phase which contains the complex. According to this method of execution of the process according to the present invention, the complex can advantageously be produced in situ in the aqueous phase by the reaction of an inorganic derivative of a metal of group 6b, hydrogen peroxide and a ligand. Once formed, the peroxo complex passes from the aqueous phase into the organic phase in which this oxidises the olefin to form aldehyde or ketone. As a result of a loss of active oxygen, the reduced complex passes then again into the aqueous phase in which it is again oxidised by hydrogen peroxyde and the cycle is thus begun once more, these cycles can repeat themselves for a long period provided the stability of the oxidised form and of the reduced form of the complex is sufficiently high. According to this embodiment of the process, it is desirable for the aqueous phase to contain a small amount of an inorganic acid.

The optimum amount of the inorganic acid to be used depends on the nature of the complex and its solubility in water in the reduced state. In general, it is such as to maintain the pH within a range of between 0.1 and 6.5.

In the case that the ligand used has only a low level of water solubility (less than 200 mmoles/liter), it can advantageously be introduced into the organic phase rather than in the aqueous phase. Under these conditions, the large surface area of contact between the two phases, which is obtained by vigorous agitation of the medium, in general gives the formation of the complex in the aqueous phase due to the limited level of dissolution of the ligand in the aqueous phase as a result of its low partition coefficient between the aqeous phase and the organic phase.

When this preferred embodiment of the process according to the present invention is carried out, the ligand must be carefully selected from among the groups mentioned above and must, in addition, and simultaneously have the following properties:

it must be capable of forming a peroxo complex with the metal of group 6b, this complex presenting a high level of solubility in the organic phase;

it must be free from affinity to the peroxo derivative in its reduced form such as to allow the return of the metal compound and the ligand from the organic phase to the aqueous phase as soon as the reduction reaction of the peroxo complex is terminated.

According to the preferred method of execution by phase transfer, the temperature and duration of the reaction can vary within wide limits and depend on the parameters described above to which the more or less substantial velocity must be added in line with which the phase transfer of the peroxo complex and its reduced form can take place. This can be determined easily by means of laboratory tests. In general, the reaction period can vary between a few minutes and several hours.

In general, it is preferred to operate at atmospheric pressure at a temperature below the boiling point of the solvent of the organic phase, at normal pressure.

The hydrogen peroxide can be used in the form of an aqueous solution. Advantageously, aqueous solutions with a low concentration can be used. Solutions containing at least 10% by weight, and preferably at least 20% by weight of hydrogen peroxide are highly advantageous. For economic reasons and for reasons of availability, solutions containing more than 90% by weight hydrogen peroxide and, more frequently, more than 70% by weight are not used.

The present invention also relates to aldehydes or ketones obtained by means of the process according to the present invention as described above.

The aldehydes and ketones according to the present invention are compounds which are used in the solvent and perfume industry and as intermediates in the synthesis of numerous organic products.

Details of the present invention are provided by the following examples which describe processes for the preparation of aldehydes and ketones according to the present invention.

First series of tests

Examples 1 and 2 relate to tests in which oxidative cleavage is carried out in the homogeneous phase in an organic medium.

EXAMPLE 1 (ACCORDING TO THE PRESENT INVENTION)

1.98 millimoles styrene were added to a solution of 5.34 millimoles active oxygen in the form of the complex of hexamethyl phosphotriamide of oxodiperoxomolybdenum ($MoO_5$-HMPT) in 50 ml 1,2-dichloroethane, the mixture was then maintained at 40° C. for 4.5 hours whereupon the reaction products were anlysed by gas chromatography. 0.35 millimoles benzaldehyde and 0.08 millimoles alpha-tolualdehyde were obtained. The degree of conversion with respect to the olefin consumed was 43%. The results are given in table 1.

EXAMPLE 2 (ACCORDING TO THE PRESENT INVENTION)

Example 1 was repeated with alpha-methylstyrene. The reaction period was 5 hours.

The results of the chromatographic analysis are given in table 2.

a quantity of sulphuric acid such as to bring the pH to 2 were added.

The mixture was then subjected to strong agitation and heated to 50° C. The temperature and agitation were maintained for 20 hours.

After cooling and slight alkalisation with 0.1N NaOH the two phases were separated.

The aqueous phase was analysed by iodometry and a peroxide consumption of 98% and a molybdate content practically equal to the amount intially introduced were determined. It was possible to recycle this aqueous phase as such after having added a fresh amount of $H_2O_2$ as necessary and after having freshly adjusted the pH to 2.

The organic phase, analysed by gas chromatography (internal standard method) indicated the formation of 12.5 millimole trans-2-butene epoxide.

EXAMPLE 4 (ACCORDING TO THE PRESENT INVENTION)

TABLE 1

| Olefin | | Active oxygen, millimoles | level of conversion of the olefin consumed, % | Products | |
|---|---|---|---|---|---|
| Type | Quantity, millimoles | | | Type | Quantity, millimoles |
| Ph—CH=CH₂ | 1,98 | 5,34 | 43 | Ph—CH(O)CH₂ (epoxide) | 0,08 |
| | | | | Ph—CHO | 0,35 |
| | | | | Ph—CH₂—CHO | 0,08 |

TABLE 2

| Olefin | | Active oxygen, millimoles | level of conversion of the olefin consumed, % | Products | |
|---|---|---|---|---|---|
| Type | Quantity, millimoles | | | Type | Quantity, millimoles |
| Ph—C(CH₃)=CH₂ | 1,30 | 2,62 | 90 | Ph—C(O)—CH₃ | 0,19 |
| | | | | Ph—CH(CH₃)—CHO | 0,63 |

Second series of tests

Examples 3 (reference) 4 and 5 (in accordance with the present invention) relate to tests in which the technique of catalysis by phase transfer is used.

EXAMPLE 3 (REFERENCE)

To a solution of 100 millimoles trans-2-butene and 1 millimole hexabutyl phosphotriamide (HBPT) in 25 ml 1,2-dicycloethane, 2 ml of an aqueous solution containing 0.5 millimoles $Na_2MoO_4$, 20.5 millimoles $H_2O_2$ and To a solution of 10 millimoles trans-beta-methylstyrene and 1 millimole tri-dodecylphosphotriamide (TDPT) in 25 ml 1,2-dichloroethane, 2 ml of an aqueous solution containing 0.5 millimoles $Na_2MoO_4$, 30 millimoles $H_2O_2$ and a quantity of sulphuric acid such as to bring the pH to 1.1 were added.

The mixture was then subjected to strong agitation and heated to 50° C. The temperature and agitation were maintained for 24 hours.

After cooling and slight alkalisation with 0.1N NaOH, the two phases were separated.

The aqueous phase was analysed by means of iodometry and a 79% peroxide consumption was found, a molybdate content practically equal to the quantity initially introduced and a quantity of unconsumed olefin of <1%. It was possible to recycle this aqueous phase as such after adding the fresh amount of $H_2O_2$ necessary and adjusting the pH to 1.1.

The organic phase which was analysed by gas chromatography (internal standard method) indicated a benzaldehyde yield, calculated on the basis of the olefin consumed, of 92% by weight. The benzaldehyde was separated from the organic phase by means of fractional distillation under vacuum. The distilled head products were solvents and excess olefin which had not been oxidised and could be recycled. The heavy distillation residue consisted mainly of TDPT and could again be used by way of appropriate purification, where necessary.

EXAMPLE 5 (ACCORDING TO THE INVENTION)

Example 4 was repeated using 10 millimoles trans-beta-methylstyrene and 20 millimoles $H_2O_2$, the amount of solvent and of $Na_2MoO_4$ remaining unchanged.

The reaction period was 24 hours at 50° C.

The level of conversion of hydrogen peroxide was 100% and that of the olefin was 70%.

In the aqueous phase, benzaldehyde was determined (yield: 69% with respect to the olefin consumed) as well as styrene oxide (yield: 14% with respect to the olefin consumed).

We claim:

1. Process for the selective production of organic aldehyde or ketone compounds from olefins comprising the steps of:
   performing an oxidative cleavage of the double bond of the olefin by means of a peroxo compound of a metal of group 6b containing a coordinated ligand, said ligand selected from the group consisting of tertiary amides, phosphoramides, aliphatic amine oxides, aromatic amine oxides, phosphine oxides and aromatic amines, the molar ratio of olefin to active oxygen of the complex being between 0.1 and 0.5 to selectively produce said aldehyde or ketone compounds free from diols and acids; and
   recovering said aldehyde or ketone compounds.

2. Process according to claim 1 characterised in that the metal is selected from among molybdenum and tungsten.

3. Process according to claim 1 characterised in that the phosphoramide is selected from among hexaethyl phosphoramide, hexaethyl phosphotriamide, hexabutyl phosphotriamide, tridodecyl phosphotriamide and octomethylpyrophosphoramide.

4. Process according to claim 1 characterised in that the amine oxide is selected from among trioctylamine and phenylpyridine oxide.

5. Process according to claim 1 characterised in that the peroxo derivative is an oxo-diperoxo compound.

6. Process according to of claim 1 characterised in that the oxidative cleavage in carried out in the homogeneous phase in an organic solvent.

7. Process according to claim 1 characterised in that the oxidative cleavage is carried out by means of the technique of phase transfer catalysis according to which, on the one hand, an organic phase not miscible with water and containing olefin is used and, on the other hand, an aqueous phase containing the complex.

8. Process according to claim 7 characterised in that the complex is formed in situ in the aqueous phase by dissolution, in this aqueous phase, of a water-soluble compound of the metal, a ligand and hydrogen peroxide.

9. Process according to claim 8 characterised in that the introduction of the ligand in the reaction medium is effected in the organic phase.

10. Process according to claim 8 characterised in that the hydrogen peroxide is used in the form of an aqueous solution containing between 10 and 90% by weight of hydrogen peroxide.

11. Process according to claim 1 characterized in that the oxidative cleavage is carried out at a temperature below the boiling point of the organic solvent at the pressure which occurs in the reaction medium.

12. Process for the oxidation of olefins to aldehydes or ketones, comprising the steps of:
    forming a coordination complex by reacting an organic ligand and a metal peroxo compound, said metal selected from group 6b, to produce a coordination complex having active oxygen; and
    reacting said complex with an olefin selected from aliphatic mono-olefines having 2 to 30 carbon atoms, cycloaliphatic mono-olefines having 4 to 20 carbon atoms, polycyclic organic compounds having ethylene bonds and polyolefins having ethylene bonds, in an organic solvent effective to dissolve the olefin and the coordination complex; wherein the molar ratio of olefin to active oxygen of the complex is between 0.1 and 0.5, to selectively produce a product free from diols and acids.

13. A process as defined in claim 1 wherein the ligand is selected from the group consisting of aliphatic amine oxides, aromatic amine oxides and phosphine oxides.

* * * * *